(12) United States Patent
Gers-Barlag et al.

(10) Patent No.: US 6,372,199 B1
(45) Date of Patent: Apr. 16, 2002

(54) USE OF UNSYMMETRICALLY SUBSTITUTED TRIAZINE DERIVATIVES IN COSMETIC OR DERMATOLOGICAL PREPARATIONS FOR MAINTAINING THE UROCANIC ACID STATUS OF THE SKIN

(75) Inventors: Heinrich Gers-Barlag, Kummerfeld; Birgit Hargens, Hamburg; Anja Müller, Rümpel, all of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/647,852
(22) PCT Filed: Apr. 16, 1999
(86) PCT No.: PCT/EP99/02581
§ 371 Date: Jan. 18, 2001
§ 102(e) Date: Jan. 18, 2001
(87) PCT Pub. No.: WO99/53895
PCT Pub. Date: Oct. 28, 1999

(30) Foreign Application Priority Data

Apr. 18, 1998 (DE) .......................... 198 17 295

(51) Int. Cl.⁷ .............................. A61K 7/42; A61K 7/44; A61K 7/00; A61K 31/53

(52) U.S. Cl. ............................ 424/59; 424/60; 424/400; 424/401; 514/241
(58) Field of Search ........................... 424/59, 60, 400, 424/401; 514/241

(56) References Cited

U.S. PATENT DOCUMENTS 5,738,842 A * 4/1998 Raspanti et al. ............... 424/59
5,759,525 A * 6/1998 Raspanti et al. ............... 424/59

* cited by examiner

Primary Examiner—Shelley A. Dodson
(74) Attorney, Agent, or Firm—Norris McLaughlin & Marcus

(57) ABSTRACT

Use of one or more unsymmetrically substituted s-triazine derivatives in cosmetic or dermatological preparations for preventing

- the washing out or washing off, caused by the action of water, of endogenous skin cis- and trans-urocanic acid from human skin or
- the washing out or washing off, caused by the action of water, of cis- and trans-urocanic acid applied artificially to the skin from human skin.

12 Claims, No Drawings

USE OF UNSYMMETRICALLY SUBSTITUTED TRIAZINE DERIVATIVES IN COSMETIC OR DERMATOLOGICAL PREPARATIONS FOR MAINTAINING THE UROCANIC ACID STATUS OF THE SKIN

The present invention relates to cosmetic and dermatological preparations containing unsymmetrically substituted triazine derivatives. In further embodiments, the present invention relates to preparations for protecting the skin against UV radiation. The invention further relates to dermatological preparations which maintain and improve the immune status of human skin.

Skin care primarily means the strengthening or rebuilding of the natural function of the skin as a barrier against environmental influences (e.g. dirt, chemicals, microorganisms) and against the loss of endogenous bodily substances (e.g. water, natural fats, electrolytes).

If this function is impaired, increased resorption of toxic or allergenic substances or attack by microorganisms can occur, leading to toxic or allergic skin reactions.

The main aim of skincare is also to compensate for the loss of sebum and water from the skin caused by daily washing. This is particularly important when the natural regeneration ability is inadequate. Furthermore, skincare products should protect against environmental influences, in particular against sun and wind, and delay the signs of skin ageing.

cis-Urocanic acid (also called cis-urocaninic acid or cis-4-imidazolylacrylic acid) is characterized by the following structural formula:

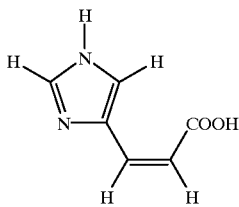

It has the empirical formula $C_6H_6N_2O_2$ and the molecular mass 138.12. cis-Urocanic acid is formed, for example, by UV irradiation of the trans isomer, which occurs in human skin and also in perspiration.

trans-Urocanic acid is characterized by the following structural formula:

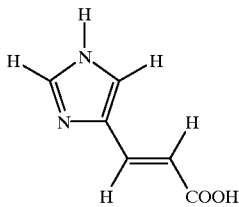

trans-Urocanic acid likewise has the empirical formula $C_6H_6N_2O_2$ and the molecular mass 138.12 and occurs in human skin and also in perspiration.

If, within the scope of the disclosure presented herein, the term "urocanic acid" is used without an indication of the isomer concerned, then both th cis and also the trans isomer and any mixtures of the two isomers are covered.

DE-A 41 21 030 shows that urocanic acid has an antiphlogistic effect, alleviates the effects of allergic reactions and prevents allergic reactions to a high degree.

Because of its antiphlogistic and antiallergic potency, urocanic acid is effective against psoriasis, neurodermatitis and contact dermatitis and autoimmune diseases, such as, for example, vitiligo, pruritus, Alopecia areata, ichthyosis and atopy, for which the activity mechanism is similar.

Traditional preparations have been unable to prevent endogenous skin urocanic acid from being washed out or washed off upon contact with water and/or surfactants or during perspiration. Even conventional preparations containing urocanic acid were at best able to freshen up the urocanic acid status of the skin a little, but no longer able to achieve the original state itself. It has hitherto only been possible to achieve this after the individual regeneration time of the skin in question.

Skincare preparations are mostly in the form of creams, lotions, milks, ointments, ointment bases, oils, tinctures, sticks, spray formulations and the like.

Customary cosmetic preparations are, for example, sunscreens. The use of trans-urocanic acid as a sunscreen is likewise known.

The harmful effect of the ultraviolet part of solar radiation on the skin is generally known. Whereas rays with a wavelength less than 290 nm (the UVC region), are absorbed by the ozone layer in the earth's atmosphere, rays in the range between 290 nm and 320 nm, the UVB region, cause an erythema, simple sunburn or even burns to the skin of greater or lesser severity.

A maximum erythema activity of sunlight is given as the narrower region around 308 nm.

Numerous compounds are known for protecting against UVB radiation; these are mostly derivatives of 3-benzylidenecamphor, of 4-aminobenzoic acid, of cinnamic acid, of salicylic acid, of benzophenone and also of 2-phenylbenzimidazole.

Also for the wavelength range between about 320 and 400 nm, the UVA region, UV filter substances are important since such rays can also cause damage. For example, it has been proven that UVA radiation leads to damage of the elastic and collagenous fibres of connective tissue, which causes the skin to age prematurely, and is to be regarded as a cause of numerous phototoxic and photoallergic reactions. The harmful effect of UVB radiation can be intensified by UVA radiation.

UV radiation can, however, also lead to photochemical reactions, in which case the photochemical reaction products intervene in the skin and cell metabolism.

Such photochemical reaction products are predominantly free-radical compounds, e.g. hydroxyl radicals, hydroperoxy radicals and superoxide ions. Undefined free-radical photoproducts which form in the skin itself can also display uncontrolled secondary reactions because of their high reactivity. However, singlet oxygen, a non-free-radical excited state of the oxygen molecule, can also be formed during UV irradiation, as can short-lived epoxides and many others. Singlet oxygen, for example, differs from normal triplet oxygen (free-radical ground state) by virtue of its increased reactivity. However, excited, reactive (free-radical) triplet states of the oxygen molecule also exist.

In order to prevent these reactions, antioxidants and/or free-radical scavengers can be additionally incorporated into the cosmetic or dermatological formulations.

Most of the inorganic pigments which are known for use in cosmetics to protect the skin against UV rays are UV absorbers or UV reflectors. These are oxides of titanium, zinc, iron, zirconium, silicon, manganese, aluminium, cerium and mixtures thereof, and modifications.

Although there are entirely advantageous cosmetic or dermatological preparations for protecting the skin against the harmful consequences of the effect of UV light, one disadvantage which is often observed is that the preparations are not water-resistant or are insufficiently water-resistant.

Sunscreen preparations are particularly frequently required and used on beaches and in open-air swimming pools. It is therefore desirable for the sunscreen formulation to be largely water-resistant so that it is not washed off from the skin or is washed off only to a small extent.

Relatively high sunscreen factors, namely, for example, those above SPF 15, can generally only be achieved using large amounts of UV filter substances. If a sunscreen product is still to have a high sunscreen factor after bathing, the UV filter substance in particular must be retained on the skin.

It is inconvenient if the sunscreen product has to be reapplied after bathing. During bathing itself, the use of a sunscreen formulation which can be washed off may, under certain circumstances, even be reckless and harmful to the skin since water does not absorb light in the UVA and UVB region very well, and consequently represents no noteworthy UV protection, not even for submerged areas of skin.

For water-resistant sunscreen formulations, the prior art usually uses non-water-soluble UV filter substances, water-repellent raw materials (e.g. silicone oils in high concentrations) and/or film formers, in particular high molecular weight compounds (e.g. PVP/hexadecene copolymers). Here, barriers are built up between the UV filter substances on the skin and the water.

A disadvantage here is that although diffusion of the filter substances into water can be delayed, it cannot be prevented completely. For this reason, such products can lose their protective effect to a considerable extent during relatively long bathing periods. However, the sun protection can be significantly diminished even as a result of the normal development of perspiration or the wiping off of this perspiration and the sunscreen substances dissolved or partially dissolved therein, in particular the endogenous skin urocanic acid, but also the artificially applied urocanic acid.

Even simple bathing in water without the addition of surfactants will initially cause the horny layer of the skin to swell, the degree of this swelling depending, for example, on the bathing time and temperature. Along with water-soluble substances, e.g. water-soluble constituents of dirt, endogenous skin substances which are responsible for the water-binding capacity of the horny layer, are also washed off or washed out. In addition, as a result of endogenous surface-active substances in the skin, fats in the skin are also dissolved and washed out to a certain extent. After the initial swelling, this causes a subsequent considerable drying-out of the skin, which can further be intensified by washing-active additives. The endogenous skin urocanic acid in particular can be washed out of the skin easily because of its high hydrophilicity.

In healthy skin, these processes are generally of no consequence since the protective mechanisms of the skin can readily compensate for such slight disturbances to the upper layers of the skin. However, even in the case of nonpathological deviations from the norm, e.g. as a result of wear damage or irritation caused by the environment, photodamage, ageing skin etc., the protective mechanism of the surface of the skin is disturbed. In some circumstances, it is then no longer able to fulfil its role by itself and must be regenerated by external measures.

Although DE-A 44 29 468 describes cosmetic and dermatological preparations containing hydrophobicized inorganic pigments for maintaining the urocanic acid status of the skin, the preparations described therein are, however, in need of improvement.

Various authors have proposed UV filter substances which have the structural formula

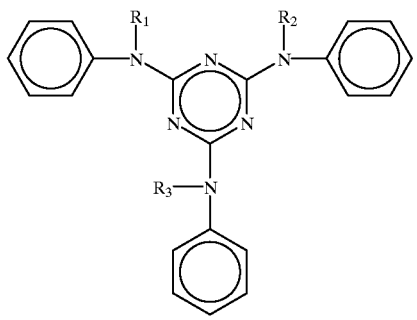

As regards the $C_3$-axis of the triazine parent substance, both symmetrical substitution and also unsymmetrical substitution are conceivable. In this sense, symmetrically substituted s-triazines have three identical substituents and are, for example, represented by tris(2-ethylhexyl) 4,4'-4''-(1,3,5-triazine-2,4,6-triyltriimino)trisbenzoate, analogously to INCI nomenclature also: octyltriazone, which is given by the following structure:

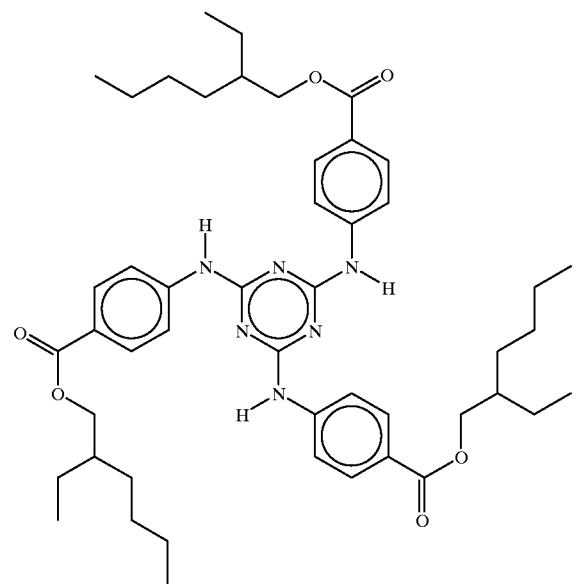

With regard to the $C_3$-axis, unsymmetrically substituted s-triazine derivatives accordingly have different substituents, as a result of which the $C_3$-symmetry is destroyed. Within the meaning of the present invention, the terms "symmetrical" and "unsymmetrical" always mean symmetrical or unsymmetrical with regard to the $C_3$-axis of the triazine parent substance, unless expressly mentioned otherwise.

For example, EP-A-570 838 describes unsymmetrically substituted s-triazine derivatives, the chemical structure of which is given by the generic formula

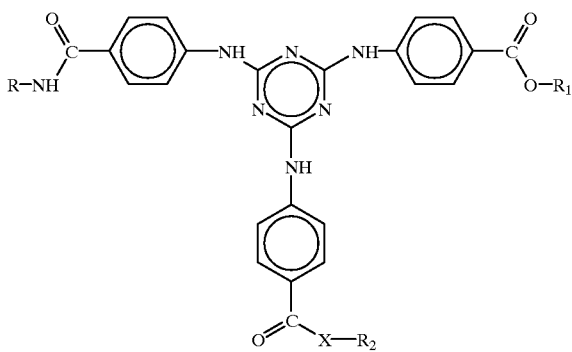

where
R is a branched or unbranched $C_1$–$C_{18}$-alkyl radical, a $C_5$–$C_{12}$-cycloalkyl radical, optionally substituted by one or more $C_1$–$C_4$-alkyl groups, X is an oxygen atom or an NH group, $R_1$ is a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

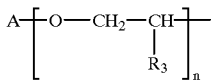

in which
A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, $R_2$ is a branched or unbranched $C_1$–$C_{18}$-alkyl radical, a $C_5$–$C_{12}$-cycloalkyl radical, optionally substituted by one or more $C_1$–$C_4$-alkyl groups, if X is the NH group, and a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

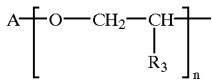

in which
A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, if X is an oxygen atom.

Such s-triazine derivatives which, in contrast to tris(2-ethylhexyl) 4,4',4"-(1,3,5-triazine-2,4,6-triyltriimino)trisbenzoate, are characterized by improved solubility in many oil components, can, according to the teaching of the specifications EP-A-821 937, EP-A-821 938, EP-A-821 939, EP-A-821 940 and EP-A-821 941, be combined with a variety of other sunscreen filters in cosmetic or dermatological preparations, whereby certain technical circumstances should be taken into account.

It was therefore an object of the present invention to remedy all of these shortcomings. In particular, the object of the invention was to provide preparations which, irrespective of whether an additional content of urocanic acid is added thereto or not, ensure that, following contact with water, the urocanic acid status of the skin is impaired as little as possible, or, in the case of an acute deficiency of urocanic acid, an almost physiological urocanic acid status is achieved. It was a further object of the present invention to provide sunscreen preparations which are characterized by a high sunscreen action and good cosmetic and dermatological acceptance.

Surprisingly, all of these objects are achieved by the use of one or more unsymmetrically substituted s-triazine derivatives in cosmetic or dermatological preparations for preventing
the washing out or washing off, caused by the action of water, of endogenous skin cis- and trans-urocanic acid from human skin or the washing out or washing off, caused by the action of water, of cis- and trans-urocanic acid applied artificially to the skin from human skin.

According to the invention, it is advantageous to choose preparations which are free from urocanic acid. It can, however, also be advantageous in some instances to use a content of cis- and/or trans-urocanic acid in preparations according to the invention.

In an advantageous embodiment, the present invention relates to the use of one or more unsymmetrically substituted s-triazine derivatives in cosmetic or dermatological preparations for preventing
the washing out or washing off, caused by the action of water, of endogenous skin cis- and trans-urocanic acid from human skin or the washing out or washing off, caused by the action of water, of cis- and trans-urocanic acid applied artificially to the skin from human skin, which is characterized in that the unsymmetrically substituted s-triazine derivative(s) is/are chosen from the group of substances whose chemical structure is given by the generic formula

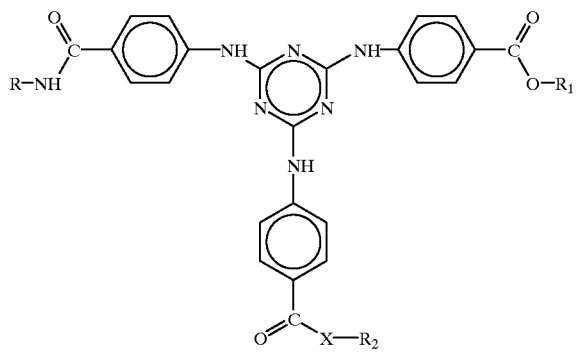

where
R is a branched or unbranched $C_1$–$C_{18}$-alkyl radical, a $C_5$–$C_{12}$-cycloalkyl radical, optionally substituted by one or more $C_1$–$C_4$-alkyl groups, X is an oxygen atom or an NH group, $R_1$ is a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

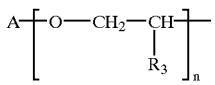

in which
A is a branched or unbranched $C_1$–$C_{18}$-alkyl radical, a $C_5$–$C_{12}$-cycloalkyl or aryl radical, optionally substituted by one or more $C_1$–$C_4$-alkyl groups,
$R_3$ is a hydrogen atom or a methyl group,
n is a number from 1 to 10,
$R_2$ is a branched or unbranched $C_1$–$C_{18}$-alkyl radical, a $C_5$–$C_{12}$-cycloalkyl radical, optionally substituted by one or more $C_1$–$C_4$-alkyl groups, if X is the NH group, and a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

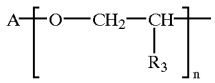

in which
A is a branched or unbranched $C_1$–$C_{18}$-alkyl radical, a $C_5$–$C_{12}$-cycloalkyl or aryl radical, optionally substituted by one or more $C_1$–$C_4$-alkyl groups,
$R_3$ is a hydrogen atom or a methyl group,
n is a number from 1 to 10,
if X is an oxygen atom.

In a preferred embodiment, the present invention relates to the use of dioctylbutylamidotriazone, the chemical structure of which is given by the formula

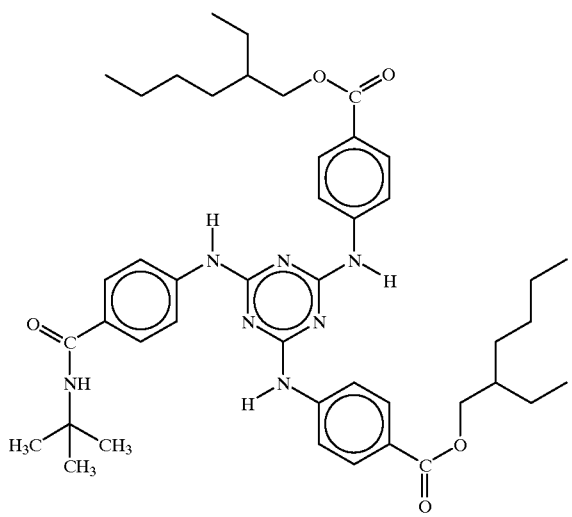

for preventing
the washing out or washing off, caused by the action of water, of endogenous skin cis- and trans-urocanic acid from human skin or
the washing out or washing off, caused by the action of water, of cis- and trans-urocanic acid applied artificially to the skin from human skin.

Medicinal topical compositions generally comprise one or more medicaments in an effective concentration. For the sake of simplicity, for clearly distinguishing between cosmetic and medicinal application and corresponding products, reference is made to the legal provisions of the Federal Republic of Germany (e.g. Cosmetics Directive, Foods and Drugs Act).

It was surprising and not to be expected by the person skilled in the art that the very s-triazine derivatives which are to be regarded as lipophilic have the properties which are advantageous according to the invention since urocanic acid, on the other hand, is certainly to be referred to as a hydrophilic substance.

Finally, it is surprising that it is unimportant for practical purposes whether the preparations according to the invention, with regard to the formulation itself, are to be considered as "water-resistant" (i.e., for example, using a defined content of water-insoluble film formers) or as "non-water-resistant" (i.e., for example, without such a content). The urocanic acid status of the skin is barely worse according to the invention without the use of film-forming preparations and following the provocative application of water than in the case of such a use of film-forming preparations.

According to the invention, it is therefore possible and in some cases particularly advantageous to dispense with a content of film formers, either lipophilic or hydrophilic film formers.

The preparations according to the invention are prepared in accordance with the customary principles familiar to the person skilled in the art. The preparations according to the invention are advantageously in the form of emulsions, advantageously W/O emulsions, preferably O/W emulsions. It is, however, also possible and in some cases advantageous according to the invention to choose other types of formulation, for example hydrodispersions, gels, oils, multiple emulsions, for example in the form of W/O/W or O/W/O emulsions, anhydrous ointments or ointment bases etc.

In simple emulsions, one phase contains finely disperse droplets of the second phase, surrounded by an emulsifier shell (water droplets in W/O emulsions or lipid vesicles in O/W emulsions). In a multiple emulsion (of the second order), on the other hand, such droplets contain finely disperse droplets of the first phase in emulsified form. Also, these droplets may in turn contain even more finely disperse droplets (multiple emulsion of the third order) and so on.

Thus, just as the terms used in the case of simple emulsions are W/O or O/W emulsions (Water-in-Oil or Oil-in-Water), the terms used in the case of multiple emulsions are W/O/W, O/W/O, O/W/O/W, W/O/W/O emulsions and so on.

Hydrodispersions are dispersions of a liquid, semisolid or solid internal (discontinuous) lipid phase in an external aqueous (continuous) phase.

However, in contrast to O/W emulsions, which are characterized by a similar phase arrangement, hydrodispersions are essentially free from emulsifiers. Hydrodispersions, like emulsions in other respects, are metastable systems and have a propensity to convert to a state of two coherent discrete phases. In emulsions, the choice of a suitable emulsifier prevents phase separation.

In the case of hydrodispersions of a liquid lipid phase in an external aqueous phase, the stability of such a system can, for example, be ensured by building up a gel structure in the aqueous phase, in which structure the lipid droplets are suspended in stable form.

The total amount of one or more unsymmetrically substituted s-triazine derivatives, in particular of dioctylbutylamidotriazone, in the finished cosmetic or dermatological preparations is advantageously chosen from the range 0.1–15.0% by weight, preferably 0.5–8.0% by weight, based on the total weight of the preparations.

Cosmetic and dermatological preparations according to the invention also advantageously comprise inorganic pigments based on metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$) or cerium (for example $Ce_2O_3$), mixed oxides of the corresponding metals and mixtures of such oxides. The pigments are particularly preferably those based on $TiO_2$.

It is particularly advantageous for the purposes of the present invention, although not absolutely necessary, if the inorganic pigments are present in hydrophobic form, i.e. have been surface-treated to repel water. This surface treatment can comprise providing the pigments with a thin hydrophobic layer by processes known per se.

Such a process comprises, for example, producing the hydrophobic surface layer by a reaction according to

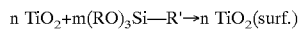

n and m here are stoichiometric parameters to be used as desired and R and R' are the desired organic radicals. Hydrophobicized pigments prepared analogously to DE-A 33 14 742, for example, are advantageous.

Advantageous $TiO_2$ pigments are obtainable, for example, under the trade names MT 100 T from TAYCA and M 160 from Kemira and T 805 from Degussa.

The cosmetic and/or dermatological sunscreen formulations according to the invention can have the customary composition and can be used for cosmetic and/or dermatological sun protection, and also for the treatment, care and cleansing of the skin and/or hair and as a make-up product in decorative cosmetics.

For use, the cosmetic and dermatological preparations according to the invention are applied to the skin and/or hair in an adequate amount in the manner customary for cosmetics.

Particularly preferred cosmetic and dermatological preparations are those which are present in the form of a sunscreen. These can advantageously additionally comprise at least one further UVA filter and/or at least one further UVB filter and/or at least one inorganic pigment, preferably an inorganic micropigment.

The cosmetic and dermatological preparations according to the invention can comprise cosmetic auxiliaries such as are usually used in such preparations, for example preservatives, bactericides, perfumes, antifoams, dyes, pigments which have a colouring action, thickeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

An additional content of antioxidants is generally preferred. According to the invention favourable antioxidants which can be used are all the antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine sulphones, penta-, hexa- and heptathionine-sulphoximine) in very low tolerated doses (for example pmol to μmol/kg), and furthermore (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof is or are the antioxidant or antioxidants, it is advantageous to choose the respective concentrations thereof from the range 0.001–10% by weight, based on the total weight of the formulation.

If vitamin A or vitamin A derivatives or carotenes or derivatives thereof is or are the antioxidant or antioxidants, it is advantageous to choose the respective concentrations thereof from the range 0.001–10% by weight, based on the total weight of the formulation.

The lipid phase can advantageously be chosen from the following group of substances:
mineral oils, mineral waxes
oils, such as triglycerides of capric or of caprylic acid, but preferably castor oil;
fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids;
alkyl benzoates;
silicone oils, such as dimethylpolysiloxanes, diethylpolysiloxanes, diphenylpoly-siloxanes and mixed forms thereof.

The oil phase of the emulsions, oleogels or hydrodispersions or lipodispersions for the purposes of the present invention is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

In addition, the oil phase can advantageously be chosen from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24, in particular 12–18 carbon atoms. The fatty acid triglycerides can, for example, be advantageously chosen from the group of synthetic, semisynthetic and natural oils, e.g. olive oil, sunflower oil, soybean oil, peanut oil, rapeseed oil, almond oil, palm oil, coconut oil, palm kernel oil and the like.

Any mixtures of such oil and wax components can also be used advantageously for the purposes of the present invention. It may also optionally be advantageous to use waxes, for example cetyl palmitate, as the sole lipid component of the oil phase.

The oil phase is advantageously chosen from the group consisting of 2-ethyhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether.

Particularly advantageous mixtures are those of $C_{12-15}$-alkyl benzoate and 2-ethylhexyl isostearate, mixtures of $C_{12-15}$-alkyl benzoate and isotridecyl isononanoate, and mixtures of $C_{12-15}$-alkyl benzoate, 2-ethylhexyl isostearate and isotridecyl isononanoate.

Of the hydrocarbons, paraffin oil, squalane and squalene are advantageously used for the purposes of the present invention.

The oil phase can also advantageously have a content of cyclic or linear silicone oils, or consist entirely of such oils, although it is preferred, apart from the silicone oil or the silicone oils, to use an additional content of other oil phase components.

Cyclomethicone (octamethylcyclotetrasiloxane) is advantageously used as silicone oil to be used according to the invention. Other silicone oils can however, also be used advantageously for the purposes of the present invention, for example hexamethylcyclotrisiloxane, polydimethylsiloxane, poly(methylphenylsiloxane).

Also particularly advantageous are mixtures of cyclomethicone and isotridecyl isononanoate, and of cyclomethicone and 2-ethylhexyl isostearate.

If appropriate, the aqueous phase of the preparations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of Carbopols, for example Carbopol grades 980, 981, 1382, 2984 and 5984, in each case individually or in combination.

Preparations according to the present invention very particularly advantageously comprise one or more surface-active substances A chosen from the group of glucose derivatives which are characterized by the structural formula

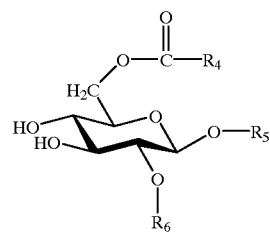

where $R_4$ is a branched or unbranched alkyl radical having 1 to 24 carbon atoms, where $R_5$ is either a hydrogen atom or a branched or unbranched alkyl radical having 1 to 24 carbon atoms, and where $R_6$ is either a hydrogen atom or a branched or unbranched acyl radical having 1 to 24 carbon atoms, and if desired one or more surface-active substances B chosen from the group of substances of the general structural formula

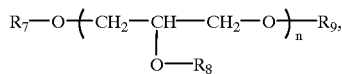

where $R_7$, $R_8$ and $R_9$, independently of one another, are chosen from the group which includes; H, branched or unbranched, saturated or unsaturated fatty acid radicals having 8 to 24 carbon atoms in which up to three aliphatic hydrogen atoms may be substituted by hydroxyl groups, and n is a number from 2 to 8.

$R_4$ is advantageously chosen from the group of unbranched alkyl radicals, preference being given to the myristyl radical, the palmityl radical, the stearyl radical and the eicosyl radical.

$R_5$ can advantageously be a hydrogen atom, but is preferably chosen from the group consisting of methyl, ethyl, propyl and isopropyl.

$R_6$ can advantageously be a hydrogen atom, but can likewise advantageously be chosen from the group consisting of myristoyl, palmitoyl, stearoyl and eicosoyl.

The surface-active substance(s) A is/are advantageously chosen from the group consisting of methylglucose monostearate (formula as below)

(A1)
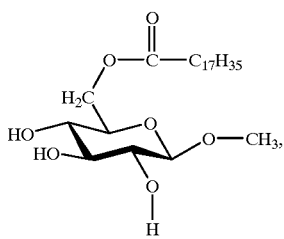

methylglucose distearate (formula as below)

(A2)
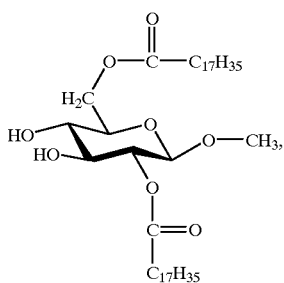

and any mixtures thereof, for example approximately equimolar mixtures thereof, which are also referred to as methylglucose sesquistearate. Such methylglucose sesquistearate is available commercially, for example under the trade name Tego® Care PS from Th. Goldschmidt KG.

The surface-active substance(s) B is/are also particularly advantageously chosen from the group of compounds in which n assumes the value 3, and $R_3$, $R_4$ and $R_5$, independently of one another, are chosen from the group which comprises: H, branched or unbranched, saturated or unsaturated fatty acid radicals having 14 to 20 carbon atoms, in particular the structures listed below:

(B1)
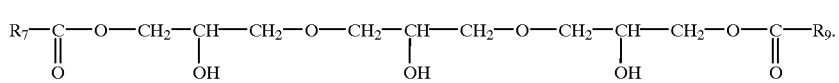

An emulsifier combination which has proven preferable according to the invention is an approximately equimolar mixture of compounds A2 and B1, where, in B1, the radicals $R_7$ and $R_9$ are preferably both a stearate radical. Such emulsifier combinations are available as "polyglyceryl(3) methylglucose distearate" (PGMS) under the trade name Tego Care® 450 from Th. Goldschmidt KG.

According to the invention, these surface-active substances A and/or B can be present in concentrations of from 0.005 to 50% by weight, based on the total weight of the preparations. Concentrations of 0.5–10% by weight, in particular 1.0–5% by weight, are preferred.

The cosmetic or dermatological sunscreen preparations advantageously comprise inorganic pigments, in particular micropigments, for example in amounts of from 0.1% by weight to 30% by weight, preferably in amounts of from 0.5% by weight to 10% by weight, but in particular from 1% by weight to 6% by weight, based on the total weight of the preparations.

It is advantageous according to the invention to use, in addition to the combinations according to the invention, oil-soluble UVA filters and/or UVB filters in the lipid phase and/or water-soluble UVA filters and/or UVB filters in the aqueous phase.

The sunscreen formulations according to the invention can advantageously comprise further substances which absorb UV radiation in the UVB region, the total amount of filter substances being, for example, from 0.1% by weight to 30% by weight, preferably 0.5 to 10% by weight, in particular 1 to 6% by weight, based on the total weight of the preparations, in order to provide cosmetic preparations which protect the skin from the entire range of ultraviolet radiation. They can also be used as sunscreens.

The further UVB filters can be oil-soluble or water-soluble. Advantageous oil-soluble UVB filter substances are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

esters of cinnamic acid, preferably 2-ethylhexyl 4-methoxycinnamate and isopentyl 4-methoxycinnamate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate.

Examples of very particularly advantageous water-soluble UVB filter substances are:

salts of 2-phenylbenzimidazole-5-sulphonic acid, such as its sodium, potassium or triethanolammonium salt, and the sulphonic acid itself, which is characterized by the following structure:

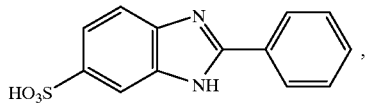

sulphonic acid derivatives of benzophenones, preferably 2-hydroxy-4-methoxybenzophenone-5-sulphonic acid and salts thereof, for example the corresponding sodium, potassium or triethanolammonium salt, where 2-hydroxy-4-methoxybenzophenone-5-sulphonic acid is characterized by the following structure:

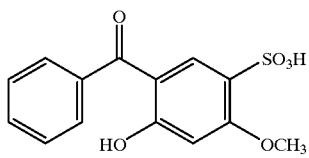

sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)sulphonic acid and salts thereof, for example the corresponding sodium, potassium or triethanolammonium salt, where 4-(2-oxo-3-bornylidenemethyl)benzenesulphonic acid is characterized by the following structure:

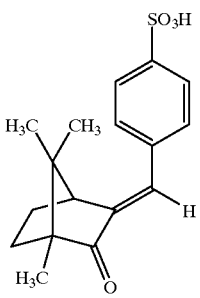

2-methyl-5-(2-oxo-3-bornylidenemethyl)benzenesulphonic acid is characterized by the following structure:

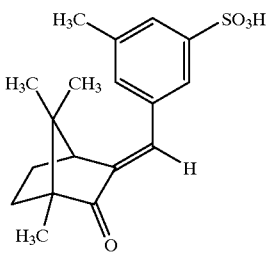

1,4-di(2-oxo-10-sulpho-3-bornylidenemethyl)benzene and salts thereof (the corresponding 10-sulphato compounds, for example the corresponding sodium, potassium or triethanolammonium salt), also referred to as benzene-1,4-di(2-oxo-3-bornylidenemethyl-10-sulphonic acid, where the parent sulphonic acid is characterized by the following structure:

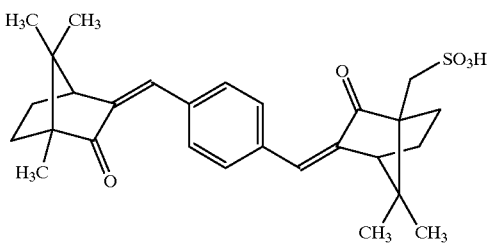

Very particularly advantageous embodiments of the present invention thus relate to the use of one or more unsymmetrically substituted s-triazine derivatives in cosmetic or dermatological preparations for preventing the washing out or washing off, caused by the action of water, of endogenous skin cis- and trans-urocanic acid from human skin or the washing out or washing off, caused by the action of water, of cis- and trans-urocanic acid applied artificially to the skin from human skin, characterized in that the preparations further comprise one or more UV filter substances which carry one or more sulphonic acid groups or sulphonate groups on their molecular backbone.

The list of further UVB filters mentioned which can be used in combination with the active ingredient combinations according to the invention is not of course intended to be limiting.

It may also be advantageous to combine the combinations according to the invention with further UVA filters which have hitherto customarily been present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. These combinations and preparations which comprise these combinations are also provided by the invention. The amounts used for the UVB combination can be employed.

It is furthermore advantageous to combine the active ingredient combinations according to the invention with further UVA and/or UVB filters.

In particular, it is advantageous to choose thickeners from the group of polyoxyethylene/polyoxypropylene block copolymers. Such block copolymers are known under the name "poloxamers" and are characterized by the following structure:

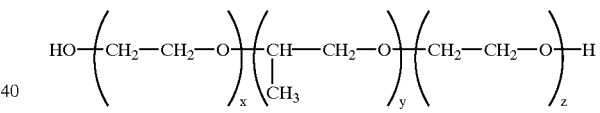

Here, x is advantageously a value between 2 and 20. y is advantageously a value between 10 and 50. z is advantageously a value of between 2 and 20.

The examples below serve to illustrate the present invention without limiting it. Unless stated otherwise, all amounts, proportions and percentages are based on the weight and the total amount or on the total weight of the preparations.

EXAMPLE 1

|  | % by weight |
|---|---|
| Methylglucose sesquistearate | 5.00 |
| Caprylic/capric triglyceride | 10.00 |
| $C_{12-15}$-alkyl benzoate | 5.00 |
| Dicaprylyl ether | 5.00 |
| Silicone oil | 1.00 |
| Dioctylbutylamidotriazone | 6.00 |
| Xanthan gum | 0.40 |
| Glycerol | 3.00 |
| Dyes, preservatives | q. s. |
| Water | ad 100.00 |

EXAMPLE 2

|  | % by weight |
|---|---|
| Polyglyceryl(3) methylglucose distearate | 4.00 |
| Sorbitan monostearate | 2.00 |
| Caprylic/capric triglyceride | 5.00 |
| $C_{12-15}$-alkyl benzoate | 5.00 |
| Dicaprylyl ether | 5.00 |
| Silicone oil | 1.00 |
| Dioctylbutylamidotriazone | 4.00 |
| t-Butylphenylmethoxyphenylpropanedione | 2.00 |
| Octyltriazone | 2.00 |
| 4-Methylbenzylidenecamphor | 3.00 |
| Sodium 2-hydroxy-4-methoxybenzophenone-5-sulphonate | 2.00 |
| Sodium hydroxide solution | 0.30 |
| Xanthan gum | 0.20 |
| Carbomer | 0.20 |
| Glycerol | 5.00 |
| Butylene glycol | 5.00 |
| Glycine | 1.00 |
| Dyes, preservatives | q. s. |
| Water | ad100.00 |

EXAMPLE 3

|  | % by weight |
|---|---|
| Polyglyceryl(3) methylglucose distearate | 3.00 |
| Sorbitan monostearate | 1.00 |
| Caprylic/capric triglyceride | 5.00 |
| 2-Octyldodecanol | 5.00 |
| Dioctylbutylamidotriazone | 4.00 |
| $TiO_2$ | 2.00 |
| Sodium hydroxide solution | 0.30 |
| Carbomer | 0.30 |
| Glycerol | 10.00 |
| Dyes, preservatives | q. s. |
| Water | ad100.00 |

EXAMPLE 4

|  | % by weight |
|---|---|
| Methylglucose sesquistearate | 3.00 |
| Polyglyceryl(3) methylglucose distearate | 3.00 |
| $C_{12-15}$-alkyl benzoate | 8.00 |
| Dicaprylyl ether | 5.00 |
| Silicone oil | 1.00 |
| Dioctylbutylamidotriazone | 6.00 |
| Urocanic acid | 1.00 |
| Sodium hydroxide solution | 0.20 |
| Xanthan gum | 0.10 |
| Carbomer | 0.20 |
| Butylene glycol | 5.00 |
| Glycine | 1.00 |
| Dyes, preservatives | q. s. |
| Water | ad100.00 |

EXAMPLE 5

|  | % by weight |
|---|---|
| Polyglyceryl(3) methylglucose distearate | 5.00 |
| Caprylic/capric triglyceride | 3.00 |

-continued

|  | % by weight |
|---|---|
| 2-Octyldodecanol | 3.00 |
| Dicaprylyl ether | 3.00 |
| Silicone oil | 1.00 |
| Dioctylbutylamidotriazone | 4.00 |
| t-Butylphenylmethoxyphenylpropanedione | 1.50 |
| $TiO_2$ | 2.00 |
| Sodium 2-hydroxy-4-methoxybenzophenone-5-sulphonate | 2.00 |
| Sodium hydroxide solution | 0.70 |
| Carbomer | 0.40 |
| Glycerol | 3.00 |
| Glycine | 1.00 |
| Dyes, preservatives | q. s. |
| Water | ad100.00 |

What is claimed is:

1. Method of preventing the loss of cis- and trans-urocanic acid from human skin said method comprising applying to the skin an effective amount therefor of a cosmetic or dermatological preparation comprising one or more unsymmetrically substituted s-triazine derivatives.

2. The method according to claim 1, wherein said one or more unsymmetrically substituted s-triazine derivatives are selected from the group consisting of compounds of the formula

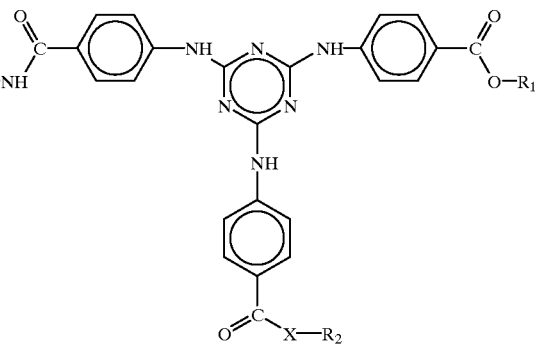

wherein
R is a branched or unbranched $C_1$–$C_{18}$-alkyl radical, a $C_5$–$C_{12}$-cycloalkyl radical, optionally substituted by one or more $C_1$–$C_4$-alkyl groups,
X is an oxygen atom or an NH group,
$R_1$ is a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

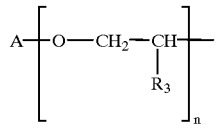

wherein
A is a branched or unbranched $C_1$–$C_{18}$-alkyl radical, a $C_5$–$C_{12}$-cycloalkyl or aryl radical, optionally substituted by one or more $C_1$–$C_4$-alkyl groups,
$R_3$ is a hydrogen atom or a methyl group,
n is a number from 1 to 10,
$R_2$ is a branched or unbranched $C_1$–$C_{18}$-alkyl radical, a $C_5$–$C_{12}$-cycloalkyl radical, optionally substituted by one or more $C_1$–$C_4$-alkyl groups, if X is the NH group, or a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

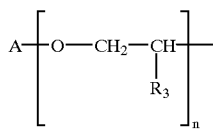

wherein

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, if X is an oxygen atom.

3. The method according to claim 1, wherein said one or more unsymmetrically substituted triazine derivatives is dioctylbutylamidotriazone.

4. The method according to claim 1, wherein the total amount of said one or more unsymmetrically substituted s-triazine derivatives, in said cosmetic or dermatological preparation is 0.1–15.0% by weight, based on the total weight of the preparation.

5. The method according to claim 1, wherein the total amount of said one or more unsymmetrically substituted s-triazine derivatives, in said cosmetic or dermatological preparation is 0.5–8.0% by weight, based on the total weight of the preparation.

6. The method according to claim 3, wherein the total amount of said dioctylbutylamidotriazone is 0.1–15.0% by weight, based on the total weight of the preparation.

7. The method according to claim 3, wherein the total amount of said dioctylbutylamidotriazone is 0.5–8.0% by weight, based on the total weight of the preparation.

8. The method according to claim 1, wherein said cosmetic or dermatological preparation further comprises urocanic acid.

9. The method according to claim 8, wherein the total amount of said urocanic acid is 0.00001 mg/ml–60.0 mg/ml, based on the total volume of said preparation.

10. The method according to claim 8, wherein the total amount of said urocanic acid is 0.05 mg/ml–1.0 mg/ml, based on the total volume of said preparation.

11. The method according to claim 1, wherein said cosmetic or dermatological preparation further comprises one or more UV filter substances which carry one or more sulphonic acid groups or sulphonate groups on their molecular backbone.

12. The method according to claim 1, wherein said cosmetic or dermatological preparation further comprises polyglyceryl(3) methylglucose distearate.

* * * * *